US00PP33296P2

(12) United States Plant Patent
Hansen

(10) Patent No.: US PP33,296 P2
(45) Date of Patent: Jul. 27, 2021

(54) ***HOSTA* PLANT NAMED 'TRENDSETTER'**

(50) Latin Name: ***Hosta* hybrid (Tratt.)**
Varietal Denomination: Trendsetter

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/974,297

(22) Filed: Dec. 18, 2020

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
See application file for complete search history.

(56) References Cited

PUBLICATIONS http://www.plantsgalore.com/Hostas/cultivars/T/Hosta_Trendsetter.htm Retrieved from the Internet on Mar. 30, 2021. (3 pages total).*

* cited by examiner

*Primary Examiner* — Susan McCormick Ewoldt

(57) ABSTRACT

A new and distinct *Hosta* plant named 'Trendsetter' of medium-sized, arching, long, ovate, medium-green leaves having wavy, yellow, jagged margins with numerous feathering intermediate colors and a narrowly acute curling apex. The flowers are pale lavender beginning in mid-June. 'Trendsetter' is attractive and is useful in the landscape, as a specimen or en masse or as a container plant.

2 Drawing Sheets

Botanical classification: *Hosta* hybrid (Tratt.).
Variety denomination: 'Trendsetter'.

STATEMENT REGARDING PRIOR DISCLOSURES UNDER 37 CFR 1.77(B)(6)

*Hosta* 'Trendsetter' was first introduced by the inventor as a non-enabling description through The American *Hosta* Society which is the International Cultivar Registration Authority registration in early 2020. No plants of *Hosta* 'Trendsetter' have been sold, in this country or anywhere in the world, nor has any disclosure of the new plant been made, more than one year prior the filing date of this application.

BACKGROUND AND ORIGIN OF THE PLANT

The present invention relates to a new and distinct *Hosta* plant, *Hosta* 'Trendsetter' hereinafter also referred to as the new plant or by the cultivar name, 'Trendsetter'. *Hosta* 'Trendsetter' was a cross by the inventor between two non-patented, unreleased, proprietary hybrids on Jun. 14, 2012 at a wholesale perennial nursery in Zeeland, Mich., USA. The female parent was identified as a proprietary, unreleased sport known only as "streaked 'Niagara Falls'" (not patented) and the male parent was 'Empress Wu' U.S. Plant Pat. No. 20,774. The new plant was assigned the breeder code 12-115-7 and passed the initial evaluation in the summer of 2014. It has been asexually propagated by division at the same nursery since 2017 and also by careful shoot tip plant tissue culture with the resultant asexually propagated plants having retained all the same traits as the original plant. *Hosta* 'Trendsetter' is stable and reproduces true to type in successive generations of asexual reproduction.

There are nearly 7,000 registered and established *Hosta* cultivars with The American *Hosta* Society, which is the International Cultivar Registration Authority for the genus *Hosta*. Several of these have green leaf blades with variegated margins. The most similar *Hosta* cultivars known to the applicant are 'Wu-La-La' U.S. Plant Pat. No. 31,309, 'Drop-dead Gorgeous' copending U.S. Plant Patent Application, 'Bridal Falls' U.S. Plant Pat. No. 22,413, 'All that Jazz' (not patented), 'Mardi Gras' (not patented) and 'Gone with the Wind' (not patented).

'Wu-La-La' has larger, rounder, flatter leaves and thinner variegated margins that are more creamy-colored. 'Seducer' has a flatter leaves with less wavy margins and there is frequently a lighter white line between the margin variegation and center. 'Drop-dead Gorgeous' is larger in habit with wider variegation. 'Bridal Falls' has a more cascading habit with leaves that are more deeply impressed veins and the variegated margin become more creamy-white. 'All that Jazz' has broader leaves that are more heart-shaped and the variegated margins is narrower. 'Mardi Gras' has broader, more heart-shaped leaves with wider margins of creamy white becoming white. 'Gone with the Wind' has narrower variegated margins and more narrow upright habit.

The female parent has leaves with random streaked variegation in the margin and a center of green and cream with wavy leaf margins and deeply impressed veins. The male parent has a larger habit and leaves of medium green having smoother veins and lack the wavy margins that are not variegated.

Other *Hosta* cultivars may have ovate leaf blades with yellow variegated margins and blue-green centers, thick leaf substance or other individual traits similar to 'Trendsetter' but the new plant differs from the above listed cultivars and all other *Hostas* known to the applicant, by the combination of the following traits.

1. Large cordate leaves of medium green, with slightly twisted acute apices and cordate base;
2. Leaves have a wavy, jagged, yellow margin and a narrowly acute curling apex;
3. Flowers are pale lavender beginning in mid-June for about four and a half weeks;
4. Medium-size mounded habit useful in the garden as edging or border, as a specimen or en masse.

BRIEF DESCRIPTION OF THE DRAWING

The photograph of the new plant demonstrates the overall appearance of the plant, including the unique traits. The colors are as accurate as reasonably possible with color reproductions. Ambient light spectrum, temperature, source and direction may cause the appearance of minor variation in color.

The drawings show a seven-year-old 'Trendsetter' plant in a trial garden at a nursery in Zeeland, Mich. with supplement fertilizer and water as needed.

DETAILED BOTANICAL DESCRIPTION

Figure 1:
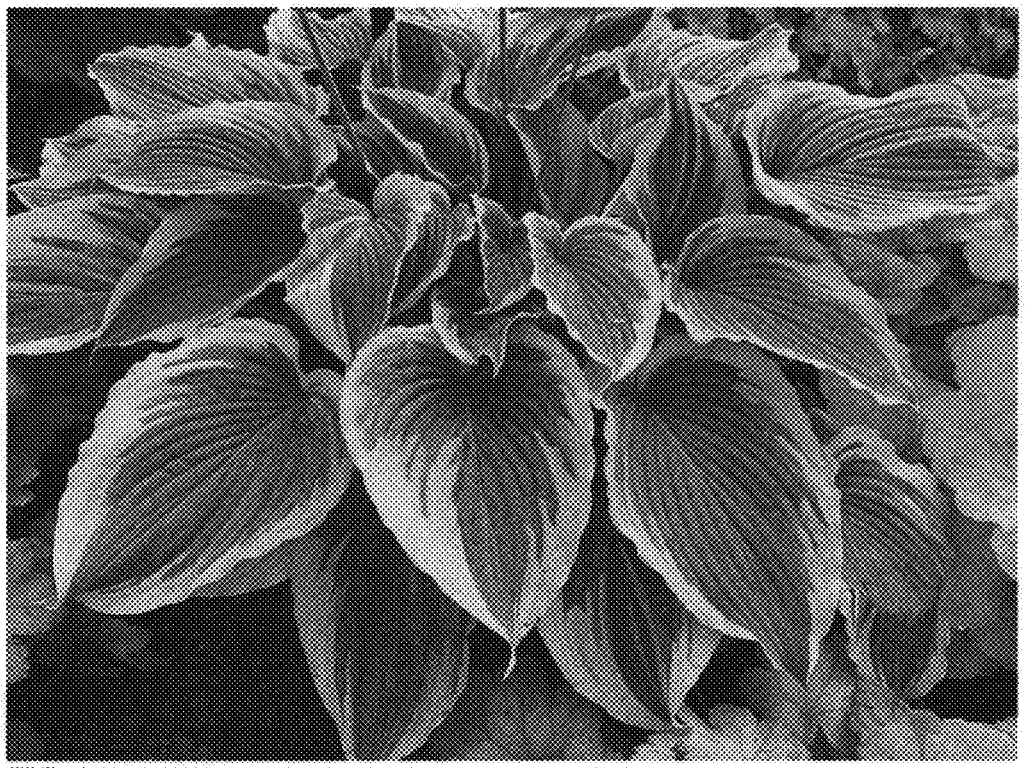
FIG. 1 shows the landscape foliage habit of a new plant just before flowering.
Figure 2:
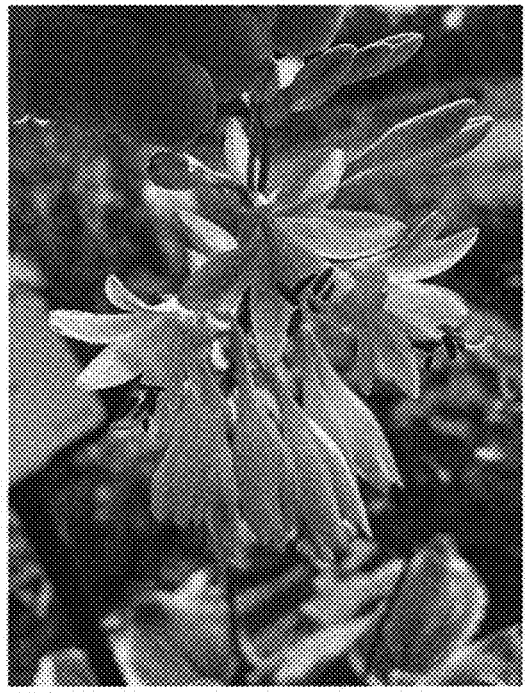
FIG. 2 shows a close-up of the flowers and buds.
Figure 3:
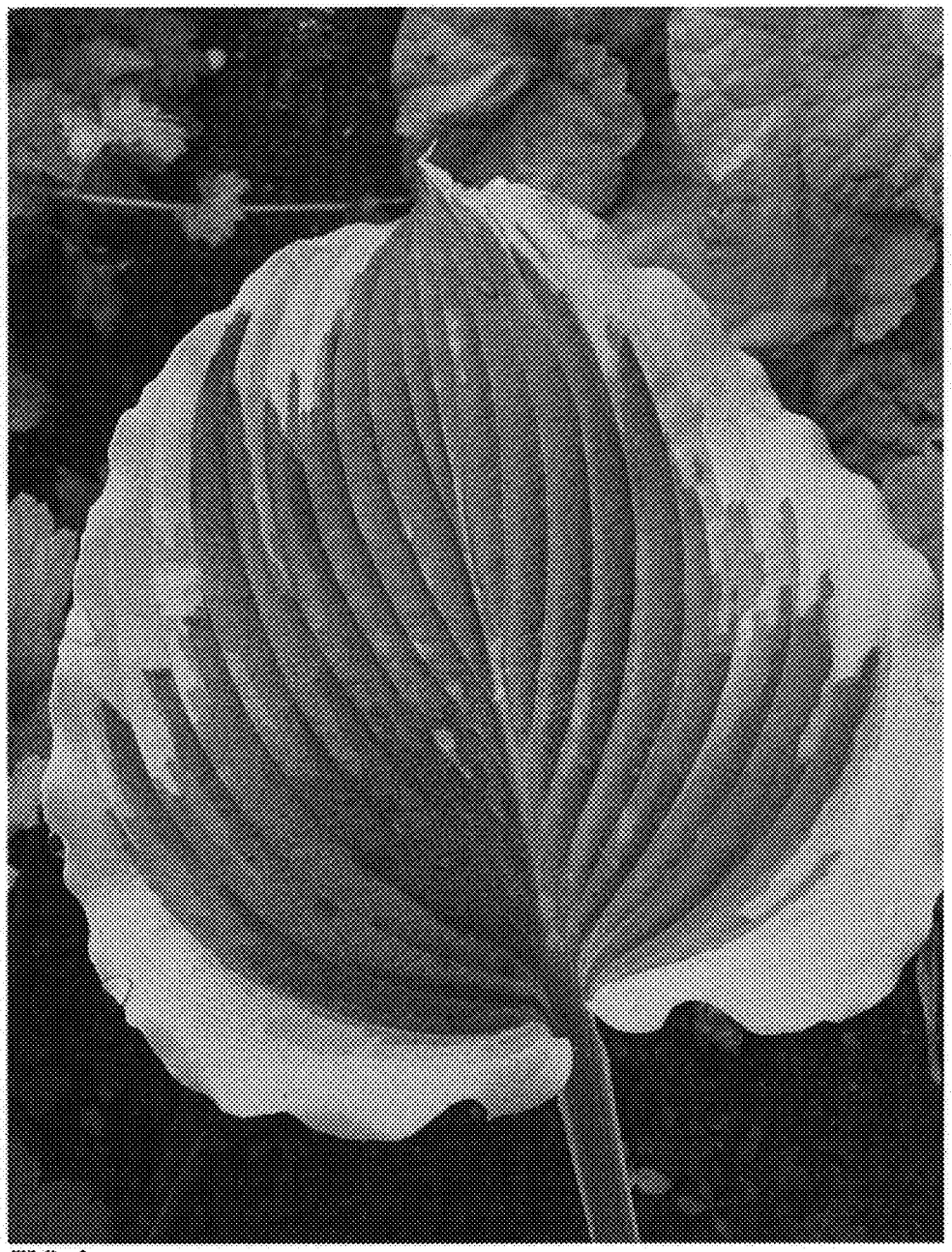
FIG. 3 shows a close-up of the foliage.

The following descriptions and color references are based on the 2015 edition of The Royal Horticultural Society Colour Chart except where common dictionary terms are used. The new plant, *Hosta* 'Trendsetter', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a seven-year-old plant in a shaded trial garden in Zeeland, Mich. with supplemental water and fertilizer.

Botanical classification: *Hosta* x hybrid;

Parentage: Female or seed parent the proprietary "streaked 'Niagara Falls'"; male or pollen parent 'Empress Wu';

Propagation: Garden division and sterile shoot tip plant tissue culture;

Time to initiate roots from tissue culture: About two to three weeks;

Growth rate: Vigorous;

Crop time: About three months to four months to finish during the spring in a one-liter container from rooted tissue culture plantlet;

Rooting habit: Fleshy, lightly branching;

Root color: Nearest RHS NN155C when actively growing;

Plant shape and habit: Hardy herbaceous perennial with basal rosette of leaves emerging from rhizomes producing a medium mound of arching petioles and leaves and erect scapes flowering above foliage;

Plant size: Foliage height to about 30.5 cm above soil line to the top of the leaves, to about 83.8 cm tall to the top of the flowers and to about 101.6 cm wide at the widest point slightly above the soil line;

Foliage description: Broadly ovate; narrowly-acute curving apex, cordate base; margin entire, heavily undulate; glabrous and matte both adaxial and abaxial; flexible but stiff; smooth, not bullate; moderately impressed adaxial veins and costate abaxial veins;

Leaf blade size: To about 24.0 cm long and about 15.0 cm wide; average about 21.5 cm long and 13.0 cm wide; margin to about 3.8 cm wide;

Leaf blade color: Early season and expanding adaxial margin between RHS 160B and RHS 1C, abaxial margin nearest between RHS 160C and RHS 1D, adaxial center nearest RHS 137A and abaxial center between RHS 137B and RHS 137C, adaxial intermediate colors comprising RHS 148B, between RHS 160A and RHS 155A and between RHS 146D and RHS 145C, abaxial intermediate colors comprising RHS 146D and RHS 145A; mid-season and mature adaxial margins nearest RES 158B, abaxial margin nearest RHS 158B, adaxial center RHS 137A, abaxial center nearest RHS 137B, adaxial intermediate colors comprising RHS 148D, RHS 145C, between RHS 146D and RHS N145C, between RHS 191B and RHS 158B and between RHS 188A and RHS 148D, abaxial intermediate colors comprising RHS 145A, RHS 146D and between RHS 191B and RHS 191C;

Petiole: Glabrous and slightly glaucous both adaxial and abaxial; deeply concavo-convex proximally and more shallowly concavo-convex; stiff; to 32.0 cm long and 1.0 cm wide at base and about 0.8 cm deep near base, average about 30.0 cm long, 0.9 cm wide and 0.7 cm deep;

Petiole color: Adaxial margins about 1.0 mm wide between RHS 145D and RHS 158B, center distally nearest RHS 37B and proximally nearest RHS 146B; abaxial margins about 1.0 mm wide between RHS 145D and RHS 158B, midrib nearest RHS 145D, next to midrib nearest RHS 146C and margins nearest RHS 137B;

Veins: Twelve to thirteen pairs and midrib; parallel; moderately impressed adaxial; costate and slightly asperous abaxial;

Veins color: Young and mature adaxial midrib nearest RHS 137A primary nearest RHS 146D, abaxial midrib between RHS 145D and RHS 148D, primary nearest RHS 147C;

Flower description:

Buds one to two days prior to opening: Clavate, with rounded apex and narrow tube base; about 46.0 mm long and 10.0 mm in diameter at widest with base narrowing in basal 18.0 mm to about 3.0 mm diameter;

Bud color: Bulb between RHS 76B and RHS 76C and tube nearest RHS 76C;

Flowers: Perfect; flared campanulate; outwardly to slightly drooping; to 54.0 mm long to exserted stigma; corolla about 46.0 mm long and 44.0 mm wide at tepal apices, fused in basal 26.0 mm, free in the distal 20.0 mm; corolla tube portion 15.0 mm long and 3.5 mm diameter; decreasing distally; persists for a normal period, usually about one day on plant; flowers tightly arranged on scape;

Flowering period: Scapes remain effective with flowers beginning mid-June for about four and a half weeks; with about 40 flowers per scape; mostly secund;

Fragrance: No detectable fragrance;

Tepal: Two nearly identical sets of three, glabrous; entire margins;

*Inner set*.—About 46.0 mm long and 9.0 mm wide slightly above fusion point; fused in basal 26.0 mm; lanceolate to clavate with acute apex; margin entire with irregular blotchy 1.0 mm wide transparent border; basal 20.0 mm fused into tube.

*Inner set color*.—Vitreous in blotchy irregular pattern along distal margin; adaxial nearest RHS 85C distally and corolla tube nearest RHS 85D, abaxial nearest RHS 85D, corolla tube portion nearest RHS 85D.

*Outer set*.—About 46.0 mm long and 9.0 mm wide slightly above fusion point; fused in basal 26.0 mm; lanceolate to clavate with acute apex; entire margin without transparent border; basal 20.0 mm fused into tube.

*Outer set color*.—Adaxial nearest RHS 85C distally and corolla tube nearest RHS 85D, abaxial nearest RHS 85D, corolla tube portion nearest RHS 85D.

Gynoecium: Single; 54.0 mm long; superior;

*Style*.—Cylindrical; about 46.0 mm long, 1.0 mm diameter; curved upward 60 degrees in distal 5.0 mm; color between RHS NN155D and RHS 145D proximally and nearest RHS NN155C distally.

*Stigma*.—Puberulent; tri-lobed; about 1.2 mm across and 1.0 mm tall; color nearest RHS NN155B.

*Ovary*.—Ellipsoidal; superior; apex rounded; base rounded to truncate; longitudinally sulcate; to about 7.0 mm long and 2.5 mm diameter in middle; color nearest RHS 145A.

Androecium: Six;

*Filaments*.—Six, approximately 48.0 mm long and 1.0 mm in diameter; curved upward to nearly 80 degrees in the distal 5.0 mm; color between RHS NN155D and RHS 145D proximally and nearest RHS NN155C distally.

*Anthers*.—Ellipsoidal with rounded ends; dorsifixed, longitudinally dehiscent; about 6.0 mm long and 2.0 mm wide; color prior to dehiscing variable, nearest RHS 166B and RHS 165C adaxial and abaxial.

*Pollen*.—Spherical; less than 0.1 mm long; color nearest RHS 17C.

Flower fragrance: None observed;

Peduncle: Cylindrical; usually one per mature division; about 4 per plant; glabrous, slightly glaucous; erect; to about 83.8 cm tall, and about 10.0 mm in diameter at base, average about 77.0 cm tall and 9.0 mm diameter at base;

Inflorescence: Flowering portion about 24.0 cm long and 7.0 cm wide; with pale lavender flowers and small floral bracts subtending each flower;

Peduncle color: Proximal portion below leaves nearest RHS 138B and distal portion nearest RHS 138A;

Pedicel: Variable in length; terete; glabrous; slightly lustrous; about 6.0 mm to 12.0 mm long and 2.0 mm diameter; outwardly to slightly drooping;

Pedicel color: Variable; nearest RHS 138B proximally and distally nearest RHS 85C with undertone of lighter than RHS N138D;

Floral bracts: Each flower normally subtended by a single bract; ovate; acute apex and truncate clasping base; entire margin; glabrous and glaucous abaxial and adaxial; to about 14.0 mm long 7.0 cm wide, decreasing distally; persisting while flowers open;

Bract color: Distal adaxial and abaxial between RHS 146D and RHS 145B with strong longitudinal blushing of RHS 79D, with narrow margins nearest RHS NN155B;

Fruit: Tri-valved dehiscent capsule; ellipsoidal to cylindrical with apex apiculate to acute and attenuate base; about 32.0 mm long and 8.0 mm diameter;

Fruit color: Nearest RHS 138B as maturing and RHS 161D when ripe;

Seed: Typically about 30 per capsule; endospermic; flattened-ellipsoidal wing surrounding embryo at one end of ellipse; to about 7.0 mm long, 3.0 mm wide and 1.5 mm thick at embryo; Seed color: nearest RHS 202A;

Disease resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars.

Growth conditions: The plant grows best and shows best coloration with plenty of moisture, adequate drainage and light shade, but is able to tolerate some drought when mature. Hardiness at least from USDA zone 3 through 8, and other disease resistance is typical of that of other *Hostas*.

It is claimed:

1. A new and distinct *Hosta* plant cultivar named *Hosta* 'Trendsetter' as herein described and illustrated.

* * * * *